United States Patent
George et al.

(10) Patent No.: US 11,166,658 B2
(45) Date of Patent: Nov. 9, 2021

(54) BLOOD SAMPLING SYSTEM AND METHOD

(71) Applicant: INVITAE CORPORATION, San Francisco, CA (US)

(72) Inventors: Sean Emerson George, San Francisco, CA (US); Nathan McDonald, San Francisco, CA (US); Eric Olivares, San Francisco, CA (US); Robert Evans, San Francisco, CA (US)

(73) Assignee: INVITAE CORPORATION, San Francisco, CA (US)

( * ) Notice: Subject to any disclaimer, the term of this patent is extended or adjusted under 35 U.S.C. 154(b) by 519 days.

(21) Appl. No.: 15/661,396

(22) Filed: Jul. 27, 2017

(65) Prior Publication Data

US 2018/0028102 A1    Feb. 1, 2018

Related U.S. Application Data

(60) Provisional application No. 62/368,011, filed on Jul. 28, 2016.

(51) Int. Cl.
*A61B 5/15*    (2006.01)
*A61B 5/151*   (2006.01)

(52) U.S. Cl.
CPC .... *A61B 5/150099* (2013.01); *A61B 5/15003* (2013.01); *A61B 5/15101* (2013.01);
(Continued)

(58) Field of Classification Search
USPC ....................................... 600/583
See application file for complete search history.

(56) References Cited

U.S. PATENT DOCUMENTS 4,360,016 A    11/1982 Sarrine
5,052,403 A    10/1991 Haber et al.
(Continued)

FOREIGN PATENT DOCUMENTS

EP    2070476 B1    2/2011
WO    WO 1993025153    12/1993

OTHER PUBLICATIONS mygenteel.com; product description available online at http://www.mygenteel.com.
(Continued)

*Primary Examiner* — Christian Jang
*Assistant Examiner* — Mitchell E Alter
(74) *Attorney, Agent, or Firm* — Pillsbury Winthrop Shaw Pittman LLP

(57) ABSTRACT

This disclosure relates to a system and method for drawing blood from a user by skin puncture instead of venous puncture and storing it for analysis. The system includes a receptacle configured to engage an area of skin of the user at a blood draw location and store blood drawn from the user; a lancet device disposed within the receptacle configured to puncture the skin of the user at the blood draw location; a vacuum device configured to reduce a pressure within the receptacle such that the skin at the blood draw location is drawn into the receptacle before the lancet device punctures the skin, and to enhance blood flow while blood is drawn from the user; and a housing configured to house the receptacle, the lancet device, and the vacuum device. The receptacle, the lancet device, and the vacuum device may be modular and removably coupled with the housing.

29 Claims, 8 Drawing Sheets

(52) U.S. Cl.
CPC .. *A61B 5/150351* (2013.01); *A61B 5/150358* (2013.01); *A61B 5/150786* (2013.01); *A61B 5/150839* (2013.01)

(56) References Cited

U.S. PATENT DOCUMENTS

| | | | |
|---|---|---|---|
| 5,554,153 | A | 9/1996 | Costello et al. |
| 5,788,652 | A | 8/1998 | Rahn |
| 5,908,416 | A | 6/1999 | Costello et al. |
| 6,063,039 | A * | 5/2000 | Cunningham ......... A61B 5/411 600/573 |
| 6,152,942 | A | 11/2000 | Brenneman et al. |
| 6,283,982 | B1 | 4/2001 | Levaughn et al. |
| 6,506,168 | B1 | 1/2003 | Fathallah et al. |
| 6,659,966 | B2 | 12/2003 | Essenpreis |
| 6,706,159 | B2 | 3/2004 | Moerman et al. |
| 6,733,493 | B2 | 5/2004 | Abboud et al. |
| 7,297,152 | B2 | 11/2007 | Fukuzawa et al. |
| 8,133,211 | B2 * | 3/2012 | Cavanaugh, II .. A61F 13/00059 604/313 |
| 8,231,549 | B2 | 7/2012 | Douglas et al. |
| 8,419,761 | B2 | 4/2013 | Pellegrino et al. |
| 8,529,526 | B2 * | 9/2013 | Wilkes ............. A61F 13/00059 604/304 |
| 8,636,672 | B2 | 1/2014 | Neel et al. |
| 9,289,763 | B2 | 3/2016 | Berthier et al. |
| 10,426,390 | B2 | 10/2019 | Berthier et al. |
| 10,779,757 | B2 | 9/2020 | Berthier et al. |
| 2002/0130042 | A1 * | 9/2002 | Moerman ............ A61B 5/1486 204/403.01 |
| 2002/0169393 | A1 | 11/2002 | Cunningham et al. |
| 2003/0083685 | A1 * | 5/2003 | Freeman ............ A61B 5/15178 606/181 |
| 2003/0098271 | A1 * | 5/2003 | Somack ................ B01D 61/00 210/295 |
| 2009/0029924 | A1 | 1/2009 | Strongin et al. |
| 2009/0131828 | A1 | 5/2009 | Wong et al. |
| 2010/0317935 | A1 | 12/2010 | Roe et al. |
| 2011/0105951 | A1 * | 5/2011 | Bernstein ............... A61B 5/157 600/573 |
| 2012/0271125 | A1 * | 10/2012 | Bernstein ......... A61B 5/150022 600/309 |
| 2014/0323915 | A1 * | 10/2014 | Christensen ......... A61B 5/1411 600/583 |
| 2016/0029937 | A1 * | 2/2016 | Sia .................... A61M 37/0015 600/341 |
| 2016/0113561 | A1 * | 4/2016 | Elmaleh ........... A61B 5/150984 600/575 |

OTHER PUBLICATIONS

Own Mumford "Autolet"; product description available online at http://www.owenmumford.com/us/patients-product/autolet-impression/#product-video-1).

Wet Cupping Therapy; product description video available at: https://www.youtube.com/watch?v=3RkW8FOYN8g.

* cited by examiner

BLOOD SAMPLING SYSTEM AND METHOD

CROSS-REFERENCE TO RELATED APPLICATIONS

This application claims priority and benefit of U.S. Provisional Application No. 62/368,011, filed on Jul. 28, 2016 and entitled "BLOOD SAMPLING SYSTEM AND METHOD", the contents of which is incorporated herein by reference in its entirety.

FIELD OF THE DISCLOSURE

This disclosure relates to a blood sampling system and method for drawing and storing blood from a user for analysis.

BACKGROUND

Obtaining enough high quality DNA and/or other analytes from blood without having to perform venous puncture may be difficult. While obtaining saliva or buccal samples may be alternatives to blood samples for some genetic tests, there may be a high failure rate in tests using such non-blood samples where failure may result from conditions specific to a patient and/or operating errors. Additionally, other analytes present in the blood (e.g., cell free DNA, biochemistry markers, and/or other biomarkers) may be desired for genetic testing which would not be obtainable through saliva and/or buccal samples. Moreover, conventional cutaneous blood collection methods such utilizing lancets to obtain blood from a finger-tip (e.g., blood glucose monitoring) may draw an inadequate quantity of blood required for genetic tests.

SUMMARY

The present disclosure provides systems and methods to obtain adequate quantities of blood (e.g. at least 0.5 mL) for testing, including genetic testing, without performing venous puncture, wherein the systems and methods may be utilized at home and/or outside of a clinic by a user.

One aspect of the disclosure relates to a blood sampling system configured to draw and store blood from a user for analysis. The system comprises a receptacle configured to engage an area of skin of the user at a blood draw location and store blood drawn from the user. The system further comprises a lancet device disposed within the receptacle configured to puncture the skin of the user at the blood draw location. The system further comprises a vacuum device configured to reduce a pressure within the receptacle. The vacuum device is configured such that the skin in response to the reduced pressure in the receptacle at the blood draw location is drawn inward into the receptacle before the lancet device punctures the skin. The reduced pressure provided by the vacuum device may further enhance blood flow while blood is drawn from the user. The system further comprises a housing configured to house, partially house, or connect the receptacle, the lancet device, and the vacuum device. The receptacle, the lancet device, and the vacuum device may be modular and removably coupled with the housing.

Another aspect of the disclosure relates to a method for drawing and storing blood from a user for analysis with a blood draw and storage system. The system comprises a receptacle, a lancet device, a vacuum device, a housing, and/or other components. The receptacle, the lancet device, the vacuum device, and/or other components are housed within, partially housed within, or connected by the housing. The receptacle, the lancet device, and the vacuum device may be modular and removably coupled with the housing. The method comprises engaging, with the receptacle, an area of skin of the user at a blood draw location. The method further comprises puncturing, with the lancet device, the skin of the user at the blood draw location. The method further comprises reducing, with the vacuum device, a pressure within the receptacle. The pressure within the receptacle is reduced such that the skin at the blood draw location is drawn inward into the receptacle before the lancet device punctures the skin. Furthermore, the reduced pressure within the receptacle may also enhance blood flow while blood is drawn from the user. The method further comprises storing, within the receptacle, blood drawn from the user.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
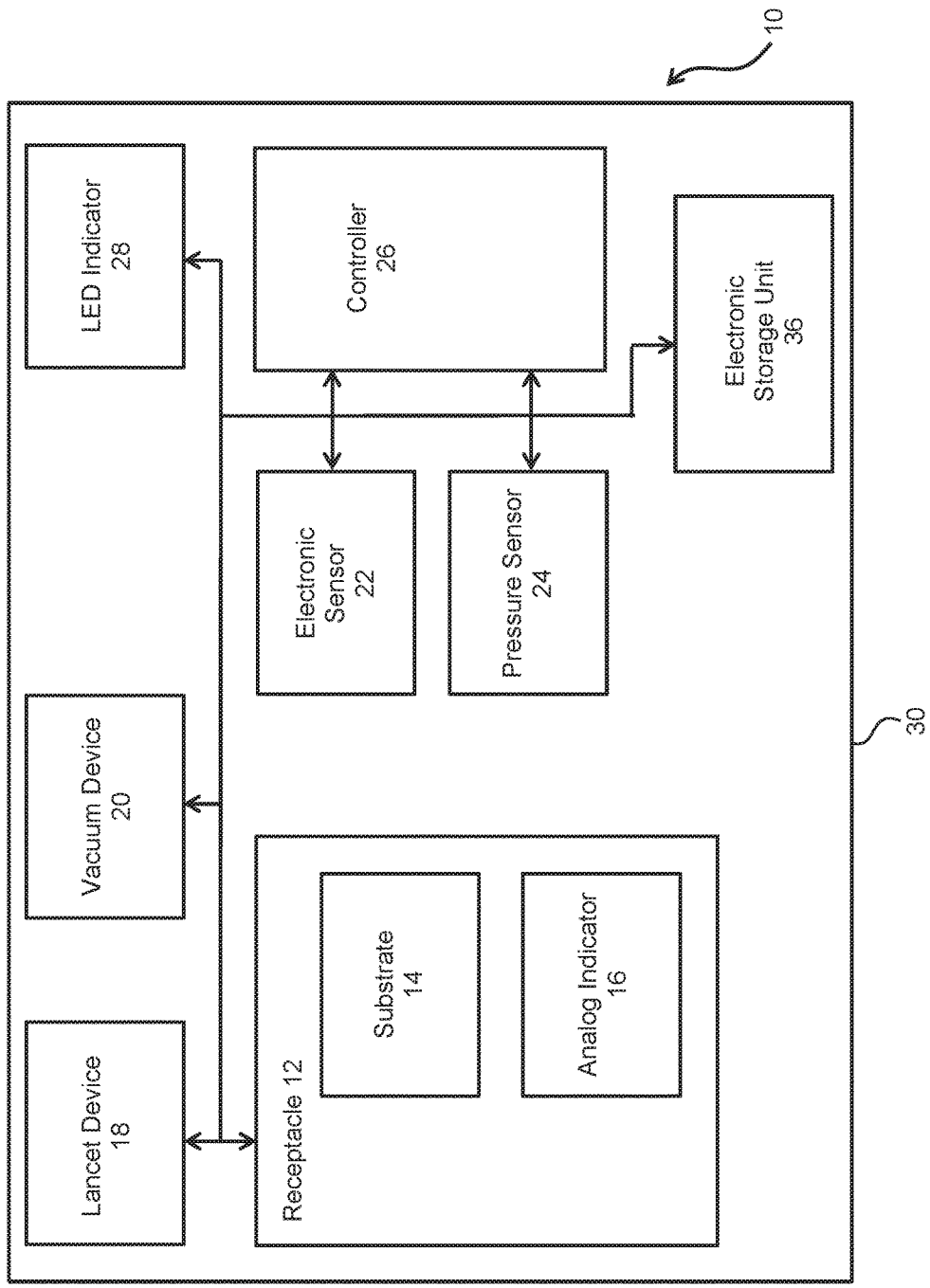
FIG. 1 illustrates a schematic of a system configured to draw and store blood from a user for analysis.

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Current solutions to obtain blood samples from a user without using a venous draw include utilizing a lancet to make an incision on the user's skin, and using a capillary tube and/or test strip to draw blood from the incision. Use of lances on a finger may be very painful and inconvenient. Other alternative lancing solutions include utilizing a laser lance. Moreover, present solutions may require immediate use of a blood sample to analyze, via blood chemistry analysis materials present on test strips, a particular biomarker. As such, present solutions may not facilitate storage and/or shipment of a blood sample to a laboratory for testing, particularly when quantities required for testing exceed 0.5 mL of blood. Accordingly, it is an object of this disclosure to provide a system and method for remote collection of blood, wherein a blood sample is immediately stabilized for shipment and/or storage.

FIG. 1 illustrates a schematic of a system 10 configured to draw and store blood from a user for analysis. In one embodiment, system 10 comprises one or more of a receptacle 12, a substrate 14, an analog indicator 16, a lancet device 18, a vacuum device 20, an electronic sensor 22, a pressure sensor 24, a controller 26, an LED indicator 28, an electronic storage unit 36, and/or other components. In some embodiments, receptacle 12, substrate 14, analog indicator 16, lancet device 18, vacuum device 20, electronic sensor 22, pressure sensor 24, controller 26, LED indicator 28, electronic storage unit 36, and/or other components may be housed by housing 30. In some embodiments, receptacle 12, substrate 14, analog indicator 16, lancet device 18, vacuum device 20, electronic sensor 22, pressure sensor 24, controller 26, LED indicator 28, and/or electronic storage unit 36 may be modular components and being housed by housing 30 is and/or includes these components being removably coupled to housing 30.

Figure 2:
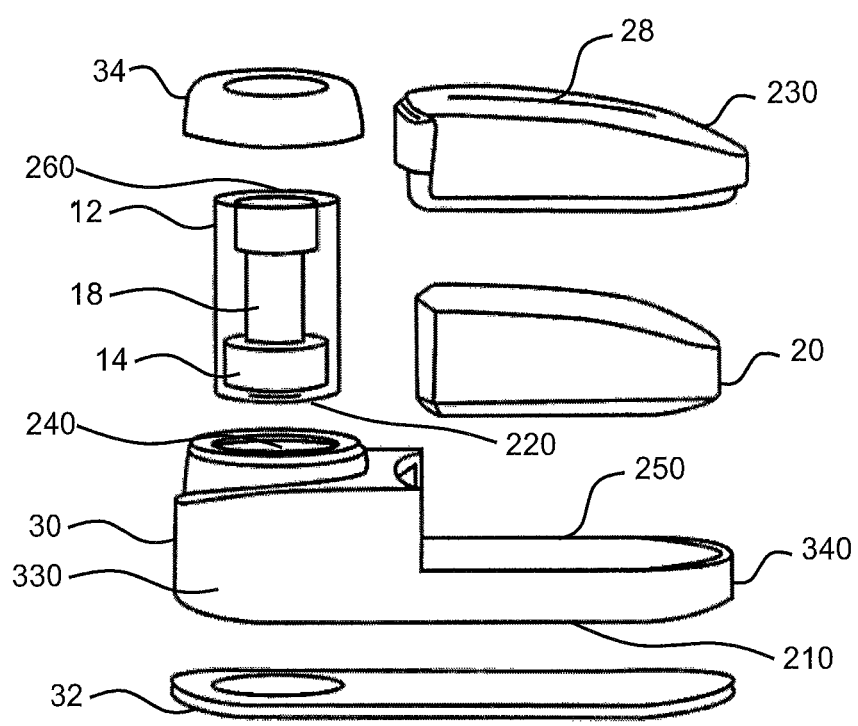
FIG. 2 illustrates modular components of the system according to one or more embodiments.
Figure 3:
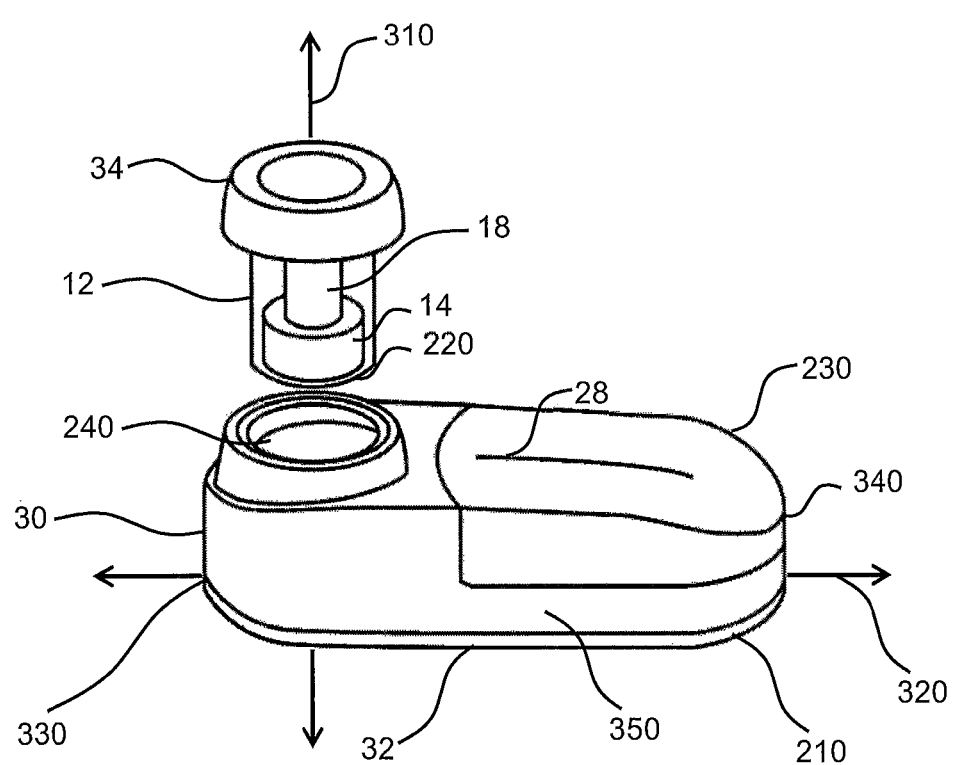
FIG. 3 illustrates a position of the receptacle and the lancet device with respect to the housing according to one or more embodiments.

Receptacle 12 is configured to engage an area of skin of the user at a blood draw location and store blood drawn from the user. In some embodiments, the blood draw location may comprise a thenar, a forearm, a shoulder, and/or other areas on the user's body. In some embodiments, receptacle 12 has a volume of at least 1 mL. In some embodiments, receptacle 12 may have a volume of at least 0.5 mL. In some embodiments, receptacle may have a volume of at least 2 mL. In some embodiments, receptacle 12 comprises one or more of glass, plastic, and/or other materials. In some embodiments, receptacle 12 comprises an opening at a first end (e.g. opening at first end 220 as illustrated in FIG. 2) such that skin of the user is drawn into the receptacle prior to and/or while blood is drawn from the user. In some embodiments, receptacle 12 comprises a second end (e.g. second end 260 as illustrated in FIG. 2), opposite the first end, wherein the second end is hermetically sealed or otherwise sealed sufficient to support reduced pressure in receptacle 12. In some embodiments, receptacle 12 forms a seal through positioning against a component of housing 30. In some embodiments, receptacle 12 is substantially transparent to facilitate the user to view blood collected. In some embodiments, receptacle 12 may have a cylindrical shape and/or any other shape facilitating modular coupling with housing 30. By way of a non-limiting example, FIGS. 2 and 3 illustrate a position of receptacle 12 with respect to housing 30 according to one or more embodiments. As shown in FIGS. 2 and 3, receptacle 12 is disposed within opening 240, between first end 330 and recessed portion 250. Moreover, as shown in FIG. 3, receptacle 12 may be positioned along first axis 310.

In some embodiments, receptacle 12 includes blood storage substrate 14 configured to absorb blood from the punctured skin. In some embodiments, substrate 14 does not cover the punctured skin of the user such that blood flow is maintained. In some embodiments, substrate 14 is toroidal shaped and positioned around lancet device 18 such that lancet device 18 punctures the skin of the user within an opening in the middle of the toroidal shape. In some embodiments, substrate 14 may include a collection media including one or more of Whatman sample collection card, FTA card, Guthrie card material, and/or other solid, liquid, or gel stabilization matrix. In some embodiments, substrate 14 is configured to stabilize nucleic acids, proteins, chemicals, and/or other blood components. In some embodiments, substrate 14 may include filter paper. In some embodiments, a diameter of the opening in a toroidal shaped substrate 14 is between about 2 mm and about 10 mm. In some embodiments, the diameter is about 3 mm and/or any other diameter. In some embodiments, receptacle 12 and/or blood storage substrate 14 are configured such that the opening in the toroidal shape is approximately centered around the wound at the blood draw location. By way of a non-limiting example, FIG. 2 illustrates modular components of system 10 according to one or more embodiments. As shown in FIG. 2, substrate 14 is disposed at or near first end 220 of receptacle 12.

Returning to FIG. 1, lancet device 18 is disposed within receptacle 12. Lancet device 18 is configured to puncture the skin of the user at the blood draw location. Lancet device 18 may be advanced to puncture the skin by any mechanical means. In some embodiments, lancet device 18 may be propelled by a spring or elastic material. In some embodiments, lancet device 18 may be propelled by a piston or motor. In some embodiments, lancet device 18 may be actuated manually by the user. In some embodiments, lancet device 18 may be automatically launched when sufficient pressure reduction is achieved in receptacle 12. Retraction of lancet device 18 may be achieved by any mechanical means, including the spring or elastic which propelled lancet device 18 forward, or a motor, piston, or other mechanism for withdrawing lancet device 18. In some embodiments, lancet device 18 may be configured such that a quantity of blood drawn from the wound created by lancet device 18 is at least 0.5 mL of blood. In some embodiments, at least 600 μL, 700 μL, 800 μL, 900 μL, 1 mL, 1.125 mL, 1.5 mL, 1.75 mL, 2.0 mL, 2.5 mL, 3 mL, or any other quantity of blood may be drawn. In some embodiments, at least 17 or 18 gauge (or any gauge supporting sufficient quantity of blood collection while minimizing user pain and time for wound closure) lancets may be provided to facilitate drawing at least 0.5 mL of blood. In some embodiments, lancet device 18 comprises multiple lancets configured to puncture the skin at the blood draw location. Multiple punctures in proximity to one another may increase blood flow. In some embodiments, the multiple punctures may be within receptacle 12 at the blood draw location. In some embodiments, the multiple punctures may be located with the opening in the middle of the toroidal shape. Pain involved in puncturing may increase marginally responsive to multiple lancets being fired simultaneously (e.g., compared to pain caused by a single lancet). Use of an 18 gauge lance on a finger may be painful and/or inconvenient, while puncturing the thenar area may be less painful. However, due to different hand sizes, wrinkles, and/or strong curvature of the tissue in the thenar area, drawing blood from the thenar may also be challenging. As such, receptacle 12, lancet device 18, and/or other components of system 10 may be configured to engage the thenar area of a user and/or other areas. In some embodiments, puncturing may be performed on a forearm of a user, since there may be fewer, but enough, blood vessels in the forearm and the puncturing may cause very little pain. In some embodiments, puncturing may be performed on a shoulder of the user as puncturing skin on a shoulder tissue may cause minimal pain. In some embodiments, at least a portion of lancet device 18 is coated with an anticoagulant coating such that healing of the wound caused by the lancing is delayed due to a temporary disruption of blood clotting caused by the anticoagulant coating. As such the wound is maintained open while blood is drawn from the user. By way of a non-limiting example, FIG. 2 illustrates lancet device 18 disposed within receptacle 12. As shown in FIG. 2, substrate 14 is toroidal shaped and positioned around lancet device 18. Furthermore, as shown in FIGS. 2 and 3, lancet device 18 may be disposed toward first end 330. Moreover, as depicted in FIG. 3, lancet device 18 may be located along first axis 310.

Returning to FIG. 1, in some embodiments, system 10 applies a vacuum to a blood draw location such that skin at the blood draw location is stretched, and the wound, caused by the lancing process, is kept open, and blood is drawn out of the user's body. Vacuum device 20 is configured to reduce a pressure within receptacle 12 (a) such that the skin at the blood draw location is drawn into receptacle 12 before the lancet device 18 punctures the skin, and (b) to enhance blood flow while blood is drawn from the user. The reduced pressure may cause the skin to form a slight dome shape inward into receptacle 12 or may cause the skin to be substantially drawn into receptacle 12. In some embodiments, vacuum device 20 comprises a motorized vacuum pump. In some embodiments, vacuum device 20 comprises a piston which may be drawn by a motor or manually to reduce pressure in receptacle 12. In some embodiments, vacuum device 20 is in fluid communication with receptacle 12. In some embodiments, the pump draws air from within receptacle 12 through an opening and/or conduit in fluid communication with receptacle 12 to reduce the pressure within receptacle 12. In some embodiments, vacuum device 20 comprises a vacuum chamber configured to reduce the pressure within receptacle 12 responsive to the vacuum chamber being pierced. In some embodiments, lancet device 18 is within receptacle 12, or in others, may travel through receptacle 12 to the skin. The reduced pressure within receptacle 12 may be ended at the completion of the blood draw by piercing or breaking the vacuum. Such piercing of the vacuum may be accomplished by mechanical means to allow air to enter receptacle 12 and raise the pressure to approximately the ambient air pressure. Such piercing may be effectuated automatically by system 10 in response to detection of adequate blood drawn or manually by the user. In some embodiments, vacuum device 20 is configured to create a pressure reduction of between 1-500 mbars, or 50-500 mbars, or 100-500 mbars, or at least 100, 150, 200, 250, 300, 350, 400, or 500 mbars within receptacle 12. As shown in FIGS. 2 and 3, vacuum device 20 may be located between first opening 240 and second end 340. Furthermore, as illustrated in FIG. 3, vacuum device 20 may be disposed along second axis 320.

Analog indicator 16 is configured to indicate of a quantity of blood in receptacle 12. In some embodiments, analog indicator 16 is configured to be visible to the user through a viewing window of receptacle 12. In some embodiments, analog indicator 16 is coupled with receptacle 12 and/or other components of system 10 in a location that facilitates a determination of the amount of blood in receptacle 12 and/or viewing of the indication provided by analog indicator 16. In some embodiments, analog indicator 16 may be and/or include a series of colored markers, a graduated cylinder, a thermometer type scale, a dial, needle, capillary tubes, filter material, narrow wick, and/or other indicators disposed within and/or in communication with receptacle 12.

Pressure sensor 24 is configured to generate output signals that convey information related to a pressure within receptacle 12. Pressure sensor 24 may be disposed within receptacle 12 such that operation of lancet device 18 is not impeded and/or obstructed. Furthermore, pressure sensor 24 may be disposed such that a blood sample stored within receptacle 12 is not contaminated and/or otherwise disturbed by pressure sensor 24. In some embodiments, pressure sensor 24 is disposed in a space between substrate 14 and the second end of receptacle 12. In some embodiments, pressure sensor 24 is coupled with other components of system 10 (e.g., controller 26) via wires and/or wirelessly.

Electronic sensor 22 is configured to generate output signals that convey information related to a quantity of blood in receptacle 12. In some embodiments, electronic sensor 12 may measure a conductivity of substrate 14 at multiple locations to determine the quantity of blood in receptacle 12. In some embodiments, electronic sensor 22 is coupled with other components of system 10 via wires and/or wirelessly.

Controller 26 is configured to provide information processing capabilities in system 10. As such, controller 26 may comprise one or more of a digital processor, an analog processor, a digital circuit designed to process information, an analog circuit designed to process information, a state machine, and/or other mechanisms for electronically processing information. Although controller 26 is shown in FIG. 1 as a single entity, this is for illustrative purposes only. In some embodiments, controller 26 may comprise a plurality of processing units. These processing units may be physically located within the same device (e.g., within housing 30), or controller 26 may represent processing functionality of a plurality of devices operating in coordination (e.g., system 10 may be wirelessly controlled by a remotely located processor.) In some embodiments, controller 26 is operatively connected to lancet device 18, vacuum device 20, LED indicator 28, pressure sensor 24, and/or electronic sensor 22. Controller 26 may be communicatively coupled with an electronic storage unit 36.

In some embodiments, controller 26 is configured to, responsive to signals received from pressure sensor 24 indicating the pressure in the receptacle breaching a predetermined pressure threshold level, cause lancet device 18 to puncture the skin of the user. In some embodiments, the pressure threshold level may be about 50, 100, 150, 200, 250, 300, 350, 400, 450, 500 mbars, or more pressure reduction relative to ambient pressure. In some embodiments, controller 26 is configured to, responsive to signals received from electronic sensor 22, determine a quantity of blood in receptacle 12. In some embodiments, controller 26 is configured to, responsive to the signals received from electronic sensor 22 indicating that a quantity of blood in receptacle 12 has breached a predetermined amount of blood, cause vacuum device 20 to cease the application of the vacuum pressure. In some embodiments, the predetermined amount of blood may be at least 500 µL, 600 µL, 700 µL, 800 µL, 900 µL, 1 mL, 1.2 mL, 1.4 mL, 1.6 mL, 1.8 mL, 2.0 mL, 2.5 mL, 3 mL, and/or other quantities of blood. In some embodiments, controller 26 is configured to cause vacuum device 20 to maintain the vacuum pressure for a predetermined amount of time, regardless of the amount of blood in receptacle 12. The predetermined amount of time may be programmed at manufacture, determined and/or adjusted by controller 26, and/or determined in other ways. The predetermined amount of time may be chosen based upon the amount of time required to draw an adequate amount of blood. In some embodiments, system 10 may draw blood into receptacle 12 until receptacle 12 is substantially full.

Electronic storage unit 36 comprises electronic storage media that electronically stores information. The electronic storage media of electronic storage unit 36 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage unit 36 may be (in whole or in part) a separate component within system 10, or electronic storage unit 36 may be provided (in whole or in part) integrally with one or more other components of system 10 (e.g., controller 26, etc.). Electronic storage unit 36 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage unit 36 may store software algorithms, information determined by controller 26, information received from electronic sensor 22, information received from pressure sensor 24, and/or other information that enables system 10 to function as described herein. By way of a non-limiting example, electronic storage unit 36 may store the predetermined pressure threshold level, blood amount, and/or other information.

In some embodiments, controller 26 is communicatively and/or operatively coupled with an LED indicator device 28. LED indicator device 28 is configured to indicate the quantity of blood in the receptacle or that an amount greater than a predetermined volume of blood is in receptacle 12. In some embodiments, responsive to controller 26 determining the quantity of blood in receptacle 12, LED indicator device 28 is caused to display a progress of blood collection. In some embodiments, controller 26 controls LED indicator device 28 to indicate amount of blood by causing LED indicator device 28 to partially/fully light up as the amount of blood received in receptacle 12 increases (such that the lighting of one or more LEDs included in LED device 28 corresponds to blood in receptacle 12). In some embodiments, LED indicator device 28 is configured to provide an indication responsive to a wound being clogged. By way of a non-limiting example, FIG. 2 illustrates LED indicator device 28 coupled with a second surface 230 of a housing 30. In some embodiments, LED indicator device 28 may be facing away from the skin during blood collection to facilitate a visible indication of an amount of blood collected. Furthermore, as illustrated in FIGS. 2 and 3, LED indicator device 28 may be located toward second end 340. Moreover, as shown in FIG. 3, LED indicator device 28 may be disposed on second surface 230, substantially parallel to second axis 320.

Returning to FIG. 1, housing 30 is configured to house, partially house, or connect receptacle 12, lancet device 18, the vacuum device 20, electronic sensor 22, pressure sensor 24, LED indicator unit 28, electronic storage unit 36, and/or other components of system 10. In some embodiments, receptacle 12, lancet device 18, vacuum device 20, electronic sensor 22, pressure sensor 24, LED indicator unit 28, electronic storage unit 36, and/or other components of system 10 are modular and/or removably coupled with housing 30. As shown in FIG. 2, receptacle 12, lancet device 18, vacuum device 20 are removably coupled with housing 30. In this example, housing 30 is shown to have a recessed portion 250 configured such that vacuum device 20 and/or other components are arranged and secured within recessed portion 250. Housing 30 may have any structure or geometry allowing for components to connect with one another and/or housing 30. In some embodiments, housing 30 may be comprised of any rigid or semi rigid material such as plastic or polymeric materials. In some embodiments, housing 30 may have an opening 240 configured such that receptacle 12, lancet device 18, and/or other components are arranged and secured within opening 240. By way of a non-limiting example, FIG. 3 illustrates a position of receptacle 12 and lancet device 18 with respect to housing 30 according to one or more embodiments. As shown in FIG. 3, housing 30 comprises a first axis 310 extending in a first direction and a second axis 320 extending in a second direction. In some embodiments, lancet device 18 and receptacle 12 are positioned along the first axis of housing 30. In some embodiments, housing 30 comprises a first end 330 adjacent to first opening 240, a second end 340, opposite first end 330, and a first side 350 between first end 330 and second end 340. In some embodiments, lancet device 18 and receptacle 12 are positioned at and/or near first end 330. Returning to FIG. 2, housing 30 comprises a first surface 210, opposite second surface 230. First surface 210 is configured to face the skin of the user while blood is drawn from the user. In some embodiments, first surface 210 is coupled to a comfort pad 32.

Figure 4:
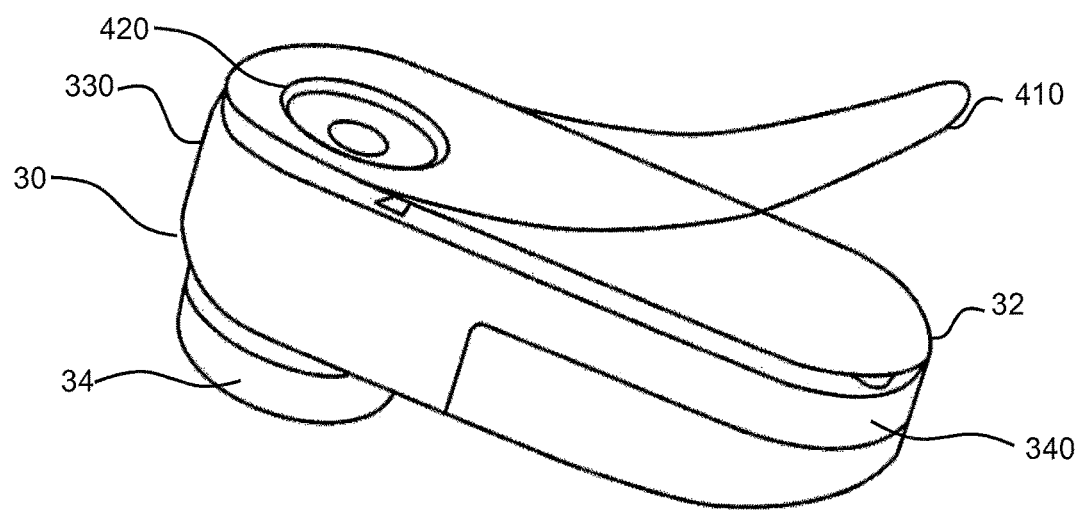
FIG. 4 illustrates a protective film covering comfort pad according to one or more embodiments.

Comfort pad 32 is configured to face the skin of the user while blood is drawn from the user. Comfort pad 32 may provide more comfort for the user while blood is drawn from the user and may ensure a better vacuum within receptacle 12. In some embodiments, comfort pad 32 may be and/or include an adhesive foam pad configured to minimize air leakage between system 10 and the skin and prevent system 10 from moving relative to the user's skin while blood is being drawn from the user. As shown in FIG. 4, comfort pad 32 comprises an opening 420 to facilitate receptacle 12 engaging the skin of the user at a blood draw location. FIG. 4 illustrates a protective film 410 covering comfort pad 32 according to one or more embodiments. In some embodiments, the user removes protective film 410 prior to placing system 10 on one of a forearm, a shoulder, or a thenar of the user.

Returning to FIG. 2, system 10 comprises a button and/or other interface device 34 configured to activate system 10. Responsive to the user placing system 10 against the skin at or near a blood draw location and then pressing (for example) button 34, vacuum device 20 (shown in FIG. 1) reduces the pressure within receptacle 12 and lancet device 18 punctures the skin of the user. Button 30 may initiate a signal which causes vacuum device 20 to begin reducing pressure in receptacle 12. In some embodiments, button 34 may initiate a mechanical action which causes vacuum device 20 to reduce pressure in receptacle 12.

Figure 5:
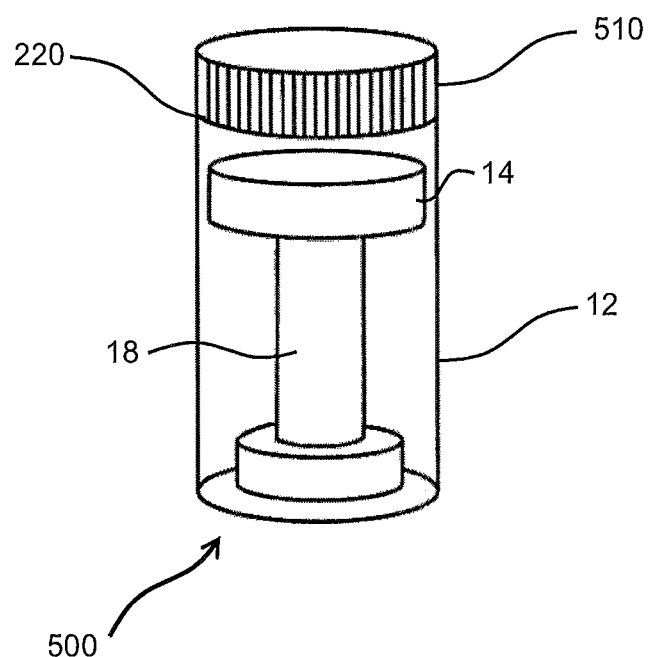
FIG. 5 illustrates a capped modular component including the receptacle, the substrate, the lancet device, and a cap according to one or more embodiments.

As shown in FIG. 2, receptacle 12 and lancet device 18 may be modular and removable from housing 30. In some embodiments, a blood sample collected may be shipped to a laboratory facility and/or stored. By way of a non-limiting example, FIG. 5 illustrates a capped modular component 500 comprising receptacle 12, substrate 14, lancet device 18, and cap 510 according to one or more embodiments. In this example, cap 510 is removably coupled with first end 220 (e.g., the end that contacts the skin of the user) of receptacle 12 to prevent blood from escaping from receptacle 12 when blood is stored in receptacle 12. Cap 510 may attach to receptacle 12 in a snap-on, screw-on fashion or an elastic fit by stretching over opening 220.

Figure 6:
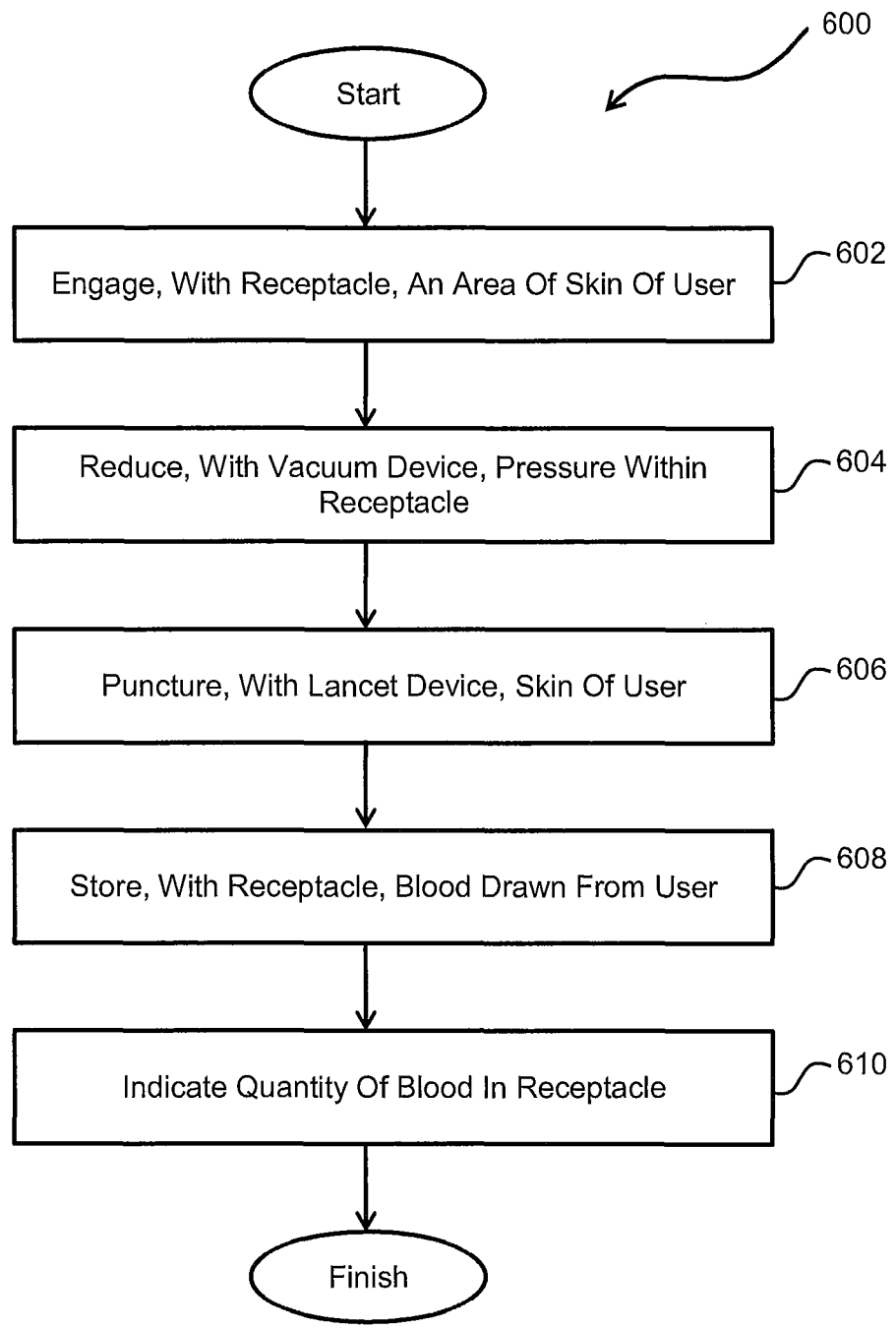
FIG. 6 illustrates a method for drawing and storing blood from a user for analysis.

FIG. 6 illustrates a method 600 for drawing and storing blood from a user for analysis with a blood drawing and storage system. The system comprises a receptacle, a lancet device, a vacuum device, a housing, and/or other components. The system may comprise any apparatus according to the invention. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

At an operation 602, an area of skin of the user at a blood draw location is engaged with the receptacle. In some embodiments, the receptacle is housed within, partially housed within, or connected with the housing. In some embodiments, the receptacle may be modular and removably coupled with the housing. In some embodiments, the receptacle has a volume of at least 1 mL. In some embodiments, the receptacle may have a volume of at least 0.5 mL, 2 mL, and/or other volumes. In some embodiments, a comfort pad is coupled with a first surface of the housing. In some embodiments, the first surface of the housing is facing the skin of the user while blood is drawn from the user. In some embodiments, the comfort pad is furnished to provide more comfort for the user while blood is drawn from the user and ensure a better vacuum within the receptacle. In some embodiments, the comfort pad may include an adhesive foam pad configured to minimize air leakage between the device and the skin and prevent device movement while blood is being drawn from the user. In some embodiments, operation 602 is performed by a receptacle the same as or similar to receptacle 12 (shown in FIG. 1 and described herein).

At an operation 604, a pressure within the receptacle is reduced with a vacuum device. In some embodiments reducing the pressure within the receptacle includes drawing the skin at the blood draw location inward into the receptacle before the lancet device punctures the skin. In some embodiments, the reduced pressure within the receptacle may enhance blood flow while blood is drawn from the user. In some embodiments, reduced pressure within the receptacle is maintained while blood is drawn from the user. In some embodiments, the vacuum device includes a motorized vacuum pump. In some embodiments, vacuum device comprises a piston which may be drawn by a motor or manually to reduce pressure in receptacle. In some embodiments, the vacuum device includes a vacuum chamber configured to reduce the pressure within the receptacle responsive to the vacuum chamber being pierced. The reduced pressure within the receptacle may be ended at the completion of the blood draw by piercing or breaking the vacuum. Such piercing of the vacuum may be accomplished by mechanical means to allow air to enter the receptacle and raise the pressure to approximately the ambient air pressure. Such piercing may be effectuated automatically by the system in response to detection of adequate blood drawn or manually by the user. In some embodiments, output signals conveying information related to the pressure within the receptacle are generated with a pressure sensor. In some embodiments, the vacuum device is housed within, partially housed within, or connected to the housing. In some embodiments, the vacuum device may be modular and removably coupled with the housing. In some embodiments, operation 604 is performed by a vacuum device the same as or similar to vacuum device 20 (shown in FIG. 1 and described herein).

At an operation 606, the skin of the user at the blood draw location is punctured with a lancet device. In some embodiments, the lancet device is caused, with a controller, to puncture the skin of the user responsive to the pressure in the receptacle breaching a threshold level. The lancet device may be advanced to puncture the skin by any mechanical means. In some embodiments, the lancet device may be propelled by a spring or elastic material. In some embodiments, the lancet device may be propelled by a piston or motor. In some embodiments, the lancet device may be actuated manually by the user. In some embodiments, the lancet device may be automatically launched when sufficient pressure reduction is achieved in the receptacle. Retraction of the lancet device may be achieved by any mechanical means, including the spring or elastic which propelled the lancet device forward, or a motor, piston, or other mechanism for withdrawing the lancet device. In some embodiments, the lancet device comprises multiple lancets configured to puncture the skin at the blood draw location. In some embodiments, at least a portion of the lancet device is coated with an anticoagulant coating. In some embodiments, the lancet device is housed within, partially housed within, or connected to the housing. In some embodiments, the lancet device may be modular and removably coupled with the housing. In some embodiments, operation 606 is performed by a lancet device the same as or similar to lancet device 18 (shown in FIG. 1 and described herein).

In some embodiments, portion of operations 604 and 606 may be performed concurrently or in an order different from what is described above such that the pressure is reduced within the receptacle prior to the lancet device puncturing the skin of the user and the reduced pressure within the receptacle is maintained while blood is drawn from the user.

At an operation 608, blood drawn from the user is stored with the receptacle. In some embodiments, at least 0.5 mL of blood is drawn from the user and stored with the receptacle. In some embodiments, at least 600 µL, 700 µL, 800 µL, 900 µL, 1 mL, 1.125 mL, 1.5 mL, 1:75 mL, 2.0 mL, 2.5 mL, 3 mL, or any other quantity of blood may be drawn. In some embodiments, storing blood drawn from the user includes absorbing, with a blood storage substrate, blood from the punctured skin. In some embodiments, the blood storage substrate is disposed within the receptacle. In some embodiments, the substrate is toroidal shaped and positioned around the lancet device such that the lancet device punctures the skin of the user within an opening in the middle of the toroidal shape. In some embodiments, the substrate does not cover the punctured skin of the user. In some embodiments, storing blood drawn from the user includes removably coupling a cap with the receptacle to prevent blood from escaping from the receptacle when blood is stored in the receptacle. In some embodiments, the cap may attach to the receptacle in a Snap-On, screw-on fashion or an elastic fit by stretching over the receptacle opening. In some embodiments, output signals conveying information related to a quantity of blood in the receptacle are generated with an electronic sensor. In some embodiments, operation 608 is performed by the receptacle as or similar to receptacle 12 (shown in FIG. 1 and described herein).

At an operation 610, the quantity of blood in the receptacle is indicated. In some embodiments, an analog indicator indicates the quantity of blood in the receptacle. In some embodiments, output signals conveying information related to a quantity of blood in the receptacle are generated with an electronic sensor. In some embodiments, operation 610 includes indicating, with an LED indicator, the quantity of blood in the receptacle responsive to the output signals generated by the electronic sensor. In some embodiments, the LED indicator may indicate that an amount greater than a predetermined volume of blood is in the receptacle. In some embodiments, operation 610 is performed by an LED indicator as or similar to LED indicator 28 (shown in FIG. 1 and described herein).

Figure 7A:
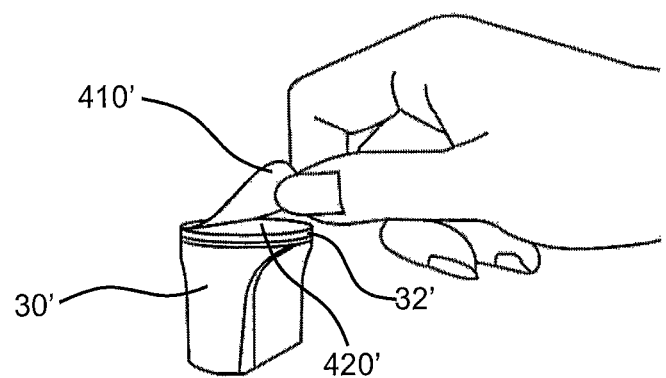
FIGS. 7a-7d illustrate a method of for drawing and storing blood from a user for analysis with a system having a vacuum chamber for reducing a pressure within the receptacle according to one or more embodiments.
Figure 7B:
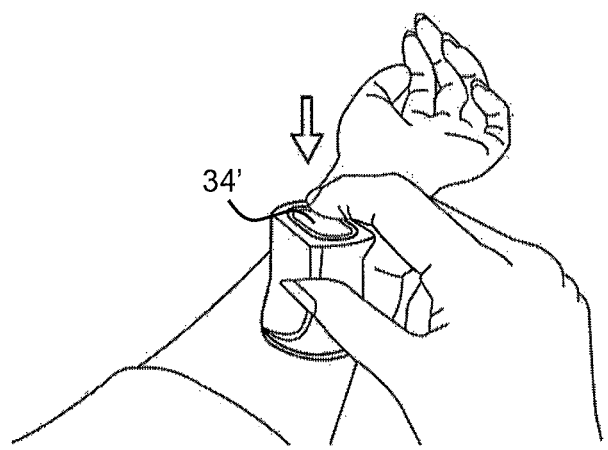
Figure 7C:
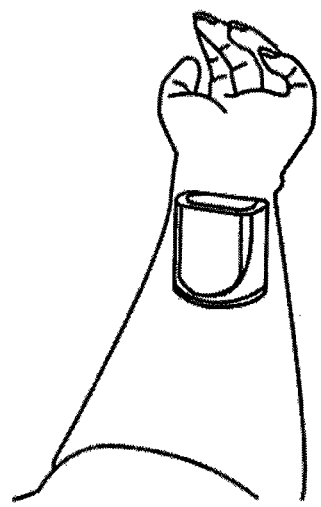
Figure 7D:
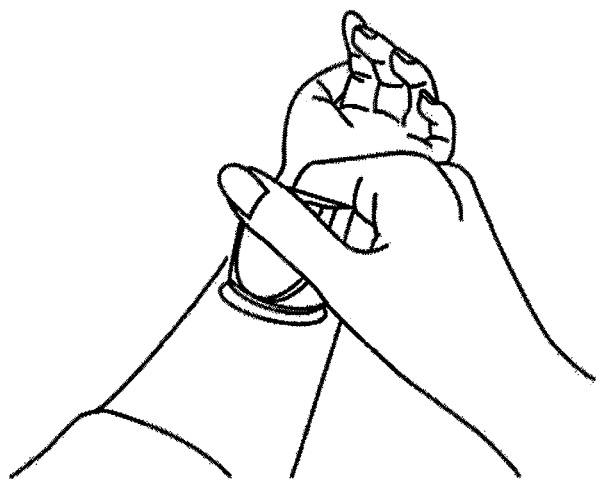

FIGS. 7a-7d illustrate a method of for drawing and storing blood from a user for analysis with a system having a vacuum chamber for reducing a pressure within the receptacle. In FIGS. 7a-7d components identified by primed reference numerals resemble similar components illustrated in FIGS. 1-4. As shown in FIG. 7a, the user removes protective film 410' covering opening 420' and adhesive foam pad 32'. Subsequent to the removal of the protective film, the user places the system on one of a forearm, a shoulder, or a thenar of the user. Next, as illustrated in FIG. 7b, responsive to the user pressing button 34', the lancet is launched causing the vacuum chamber to be pierced. Following the lancet launch and as illustrated by FIG. 7c, responsive to the vacuum chamber being pierced, a pressure within the receptacle is reduced causing the skin to be pulled into the chamber. Subsequently, the lancet device punctures the skin of the user at a blood draw location. In this example, a quantity of blood drawn in the receptacle is indicated by a manual indicator. FIG. 7d illustrates a removal procedure of the system from the user's body. In FIG. 7d the system is shown to be tilted to a side such that air is allowed in the receptacle in order to remove the system from the user's body.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and, equivalent arrangements that are within the spirit and scope of the appended claims. For example, it is to be understood that the present technology contemplates that, to the extent possible, one or more features of any implementation can be combined with one or more features of any other implementation.

What is claimed is:

1. A blood sampling system configured to draw and store blood from a user for analysis, the system comprising:
    a receptacle configured to engage an area of skin of the user at a blood draw location and store blood drawn from the user, the receptacle having a first end and a second end, the second end being opposite the first end and being sealed to support reduced pressure in the receptacle;
    a lancet device disposed within and movable within the receptacle between the first end and the second end thereof and configured to puncture the skin of the user at the blood draw location;
    a vacuum device configured to reduce a pressure within the receptacle (1) such that the skin at the blood draw location is drawn into the receptacle before the lancet device punctures the skin, and (2) to enhance blood flow while blood is drawn from the user; and
    a housing configured to house the receptacle, the lancet device, and the vacuum device, the housing having a first end and a second end and wherein the housing has a recessed portion at the second end thereof, the first end of the receptacle being configured for insertion into an opening of the housing to engage the area of skin of the user, the opening for the receptacle and the lancet device being between the first end of the housing and the recessed portion,
    wherein the lancet device and the receptacle are positioned along a first axis of the housing at the first end of the housing, the vacuum device being disposed along a second axis, the first axis extending in a first direction and the second axis extending in a second direction, the second direction being different than the first direction,
    wherein the receptacle and the lancet device are modular and removably coupled with the housing, the lancet device being removable together with the receptacle from said opening of the housing,
    wherein the vacuum device is modular and removably coupled with the housing, the vacuum device being separately removable from the recessed portion of the housing and relative to the receptacle,
    wherein the receptacle further includes a blood storage substrate therein and disposed at or near the first end thereof, the blood storage substrate being configured to absorb blood from the punctured skin, the blood storage substrate comprising a solid, liquid, or gel stabilization matrix,
    wherein the receptacle, the lancet device, and the vacuum device are configured to draw and store at least 1.0 ml of blood.

2. The system of claim 1, wherein the receptacle, the lancet device, and the vacuum device are configured to draw and store at least 1.125 ml of blood.

3. The system of claim 1, wherein a volume of the receptacle is at least 1 ml.

4. The system of claim 1, wherein the substrate does not cover the punctured skin of the user.

5. The system of claim 1, wherein the substrate is toroidal shaped and positioned around the lancet device such that the lancet device punctures the skin of the user within an opening in the middle of the toroidal shape.

6. The system of claim 1, further comprising a cap that removably couples with the first end of the receptacle to prevent blood from escaping from the receptacle when blood is stored in the receptacle.

7. The system of claim 1, wherein the lancet device includes a 17 gauge or an 18 gauge lancet.

8. The system of claim 1, wherein the lancet device comprises multiple lancets configured to puncture the skin at the blood draw location.

9. The system of claim 1, wherein at least a portion of the lancet device is coated with an anticoagulant coating.

10. The system of claim 1, wherein the vacuum device comprises a motorized vacuum pump.

11. The system of claim 1, wherein the vacuum device comprises a vacuum chamber configured to reduce the pressure within the receptacle responsive to the vacuum chamber being pierced.

12. The system of claim 1, further comprising an analog indicator of a quantity of blood in the receptacle.

13. The system of claim 1, further comprising an electronic sensor configured to generate output signals that convey information related to a quantity of blood in the receptacle.

14. The system of claim 13, further comprising an LED indicator device coupled with the housing, the LED indicator device configured to indicate the quantity of blood in the receptacle, the quantity of blood in the receptacle determined based on the output signals from the electronic sensor.

15. The system of claim 1, further comprising a pressure sensor configured to generate output signals that convey information related to a pressure within the receptacle, the pressure sensor being disposed within the receptacle between the blood storage substrate and the second end of the receptacle, the second end of the receptacle having a button thereon to initiate an action to thereby cause the vacuum device to reduce pressure within the receptacle; and a controller configured to, responsive to the pressure in the receptacle breaching a threshold level, cause the lancet device to puncture the skin of the user.

16. The system of claim 1, further comprising a comfort pad coupled with a first surface of the housing, the first surface of the housing facing the skin of the user while blood is drawn from the user.

17. The system of claim 1, wherein the stabilization matrix stabilizes nucleic acids present in a blood sample.

18. A method for drawing and storing blood from a user for analysis with a system comprising a receptacle, a lancet device, a vacuum device, and a housing, the housing having a first end and a second end and wherein the housing has a recessed portion at the second end thereof, the receptacle having a first end and a second end, the second end being opposite the first end and being sealed to support reduced pressure in the receptacle, the first end of the receptacle being configured for insertion into an opening of the housing to engage the area of skin of the user, the opening for the receptacle and the lancet device being between the first end of the housing and the recessed portion, and the lancet device disposed within and movable within the receptacle between the first end and the second end thereof, wherein the lancet device and the receptacle are positioned along a first axis of the housing at the first end of the housing, the vacuum device being disposed along a second axis, the first axis extending in a first direction and the second axis extending in a second direction, the second direction being different than the first direction; the method comprising:
engaging, with the receptacle, an area of skin of the user at a blood draw location;
puncturing, with the lancet device, the skin of the user at the blood draw location;
reducing, with the vacuum device, a pressure within the receptacle (1) such that the skin at the blood draw location is drawn into the receptacle before the lancet device punctures the skin, and (2) to enhance blood flow while blood is drawn from the user; and
storing, with the receptacle, blood drawn from the user,
wherein the storing comprises absorbing, with a blood storage substrate, blood from the punctured skin, wherein the blood storage substrate is disposed within the receptacle at or near the first end thereof and wherein the blood storage substrate comprises a solid, liquid, or gel stabilization matrix,
wherein the receptacle, the lancet device, and the vacuum device are housed within the housing and configured to draw and store at least 1.0 ml of blood during drawing of blood and said storing,
wherein the receptacle and the lancet device are modular and removably coupled with the housing, the lancet device being removable together with the receptacle from said opening of the housing, and
wherein the vacuum device is modular and removably coupled with the housing, the vacuum device being separately removable from the recessed portion of the housing and relative to the receptacle.

19. The method of claim 18, further comprising drawing and storing, with the receptacle, the lancet device, and the vacuum device, at least 1.125 ml of blood, wherein a volume of the receptacle is at least 1.125 ml.

20. The method of claim 18, wherein the substrate is toroidal shaped and positioned around the lancet device such that the lancet device punctures the skin of the user within an opening in the middle of the toroidal shape and wherein the substrate does not cover the punctured skin of the user.

21. The method of claim 18, wherein the vacuum device comprises vacuum chamber configured to reduce the pressure within the receptacle responsive to the vacuum chamber being pierced.

22. The method of claim 18, wherein the system further comprises an electronic sensor configured to generate output signals that convey information related to a quantity of blood in the receptacle.

23. The method of claim 22, further comprising indicating, with an LED indicator, the quantity of blood in the receptacle responsive to the output signals generated by the electronic sensor.

24. The method of claim 18, further comprising removably coupling a cap with the first end of the receptacle to prevent blood from escaping from the receptacle when blood is stored in the receptacle.

25. The method of claim 18, wherein the system further comprises a pressure sensor configured to generate output signals that convey information related to a pressure within the receptacle, the pressure sensor being disposed within the receptacle between the blood storage substrate and the second end of the receptacle, the second end of the receptacle having a button thereon to initiate an action to thereby cause the vacuum device to reduce pressure within the receptacle, and wherein the method further comprises initiating the vacuum device by pressing the button.

26. The method of claim 25, further comprising causing, by a controller, the lancet device to puncture the skin of the user responsive to the pressure in the receptacle breaching a threshold level.

27. The method of claim 18, wherein the lancet device comprises multiple lancets configured to puncture the skin at the blood draw location and wherein at least a portion of the lancet device is coated with an anticoagulant coating.

28. The method of claim 18, wherein the system further comprises a comfort pad coupled with a first surface of the housing, the first surface of the housing facing the skin of the user while blood is drawn from the user.

29. The method of claim 18, wherein the stabilization matrix stabilizes nucleic acids present in a blood sample.

\* \* \* \* \*